(12) United States Patent
Kimura

(10) Patent No.: US 7,317,534 B2
(45) Date of Patent: Jan. 8, 2008

(54) MEASURING METHOD AND SYSTEM

(75) Inventor: Toshihito Kimura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/246,613

(22) Filed: Oct. 11, 2005

(65) Prior Publication Data

US 2006/0077391 A1    Apr. 13, 2006

(30) Foreign Application Priority Data

Oct. 8, 2004   (JP)   ............................. 2004-296447

(51) Int. Cl.
*G01N 21/45* (2006.01)
(52) U.S. Cl. ..................................... 356/445
(58) Field of Classification Search ................. 356/445
See application file for complete search history.

(56) References Cited

U.S. PATENT DOCUMENTS

| | | | |
|---|---|---|---|
| 4,844,613 A * | 7/1989 | Batchelder et al. .......... | 356/318 |
| 5,434,663 A * | 7/1995 | Maule ......................... | 356/300 |
| 5,485,277 A | 1/1996 | Foster | |
| 5,492,840 A * | 2/1996 | Malmqvist et al. .......... | 436/518 |
| 6,417,924 B1 * | 7/2002 | Kimura ........................ | 356/445 |
| 6,956,651 B2 * | 10/2005 | Lackritz et al. ............... | 356/445 |
| 7,030,988 B2 * | 4/2006 | Kubo et al. .................. | 356/445 |
| 2005/0175999 A1 * | 8/2005 | Klakamp et al. .............. | 435/6 |
| 2005/0216205 A1 * | 9/2005 | Tsuzuki ....................... | 702/19 |
| 2006/0044563 A1 * | 3/2006 | Fujikura ...................... | 356/445 |
| 2006/0073609 A1 * | 4/2006 | Shimizu et al. ............. | 436/180 |

FOREIGN PATENT DOCUMENTS

| | | |
|---|---|---|
| JP | 6-167443 A | 6/1994 |
| WO | WO 03/056296 A2 | 7/2003 |
| WO | WO 03/056296 A3 | 7/2003 |

OTHER PUBLICATIONS

Takayuki Okamoto, "Surface Refracto-Sensor using Evanescent Waves: Principles and Instrumentations", vol. 47, No. 1, 1998, pp. 19-28.
Danny van Noort, et al., "Porous Gold in Surface Plasmon Resonance Measurement", EUROSENSORS X III, 1999, pp. 585-588.

\* cited by examiner

*Primary Examiner*—Tu T Nguyen
(74) *Attorney, Agent, or Firm*—Sughrue Mion, PLLC

(57) ABSTRACT

A measuring signal in the detecting area is calibrated on the basis of a measuring signal in the reference area by the reference method. The rate of change with time of the difference between the measuring signal and an estimated result of the measurement (ORU constant) is calculated in the period where it is expected that the signal shows a fixed value and the components which change at a rate of change calculated for the entire period of the measuring period with the instance when a buffer containing thereon an analyte is supplied taken as a reference are taken as the drift components and correction to remove the drift components from the measuring signal is carried out.

8 Claims, 12 Drawing Sheets

MEASURING METHOD AND SYSTEM

BACKGROUND OF THE INVENTION

1. Field of the Invention

This invention relates to a measuring method and a measuring system where a light beam is caused to be reflected in total internal reflection at an interface between a film layer in contact with an object to be measured such as a sample and a dielectric block to generate evanescent waves, and the change in the intensity of the light beam reflected in total internal reflection is measured to analyze the sample.

2. Description of the Related Art

As a measuring system using evanescent waves, there has been known a surface plasmon sensor. In metal, free electrons vibrate in a group to generate compression waves called plasma waves. The compression waves generated in a metal surface are quantized into surface plasmon. The surface plasmon sensor analyzes the property of the sample utilizing a phenomenon that such surface plasmon is excited by light waves. There have been proposed various types of surface plasmon sensors. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism. A metal film is formed on one face of the dielectric block and is brought into contact with a sample. A light source emits a light beam. An optical system causes the light beam to enter the dielectric block to impinge upon the interface of the dielectric block and the metal film at various angles of incidence so that total internal reflection conditions are satisfied at the interface. A photodetector means detects the intensity of the light beam reflected in total internal reflection at the interface. A measuring means detects a state of surface plasmon resonance on the basis of the result of detection of the photodetector means.

In order to obtain various angles of incidence of the light beam to the interface, a relatively thin incident light beam may be caused to impinge upon the interface while deflecting the incident light beam so that the angle of incidence changes or a relatively thick incident light beam may be caused to impinge upon the interface in the form of convergent light or divergent light so that components of the incident light beam impinge upon the interface at various angles. In the former case, the light beam which is reflected from the interface at an angle which varies as the incident light beam is deflected may be detected by a small photodetector which is moved in synchronization with deflection of the incident light beam or by an area sensor extending in the direction in which reflected light beam is moved as a result of deflection. In the latter case, the light beam which is reflected from the interface can be detected by an area sensor which extends in directions so that all the components of light reflected from the interface at various angles can be detected.

In such a plasmon resonance sensor, when a light beam impinges upon the interface at a particular angle of incidence $\theta sp$ not smaller than the angle of total internal reflection, evanescent waves having an electric field distribution in the sample in contact with the metal film are generated and surface plasmon is excited in the interface between the metal film and the sample by the evanescent waves. When the wave number vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence $\theta sp$ at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, $\omega$ represents the angular frequency of the surface plasmon, c represents the speed of light in a vacuum, and $\varepsilon_m$ and $\varepsilon_s$ respectively represent the dielectric constants of the metal and the sample.

When the dielectric constant $\varepsilon_s$ of the sample is known, the refractive index of the sample and the like can be calculated on the basis of a predetermined calibration curve and the like. Accordingly a property related to the dielectric constant $\varepsilon_s$ of the sample or the refractive index of the sample can be detected by detecting the angle of incidence $\theta sp$ at which the intensity of light reflected in total internal reflection from the interface of the prism and the metal film sharply drops (this angel $\theta sp$ will be referred to as "the attenuation angle $\theta sp$", hereinbelow).

As a similar apparatus utilizing the evanescent waves, there has been known a leaky mode sensor described in, for instance, "Surface Refracto-Sensor using Evanescent Waves: Principles and Instrumentations" by Takayuki Okamoto, Spectral Research, Vol. 47, No. 1 (1998), pp. 19-28. The leaky mode sensor basically comprises a dielectric block shaped, for instance, like a prism, a clad layer which is formed on one face of the dielectric block. An optical waveguide layer is formed on the clad layer and is brought into contact with a sample. A light source emits a light beam. An optical system causes the light beam to enter the dielectric block to impinge upon the interface of the dielectric block and the metal film at various angles of incidence so that total internal reflection conditions are satisfied at the interface. A photodetector means detects the intensity of the light beam reflected in total internal reflection at the interface. A measuring means detects a state of excitation of the waveguide mode on the basis of the result of detection of the photodetector means.

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence θsp at which the attenuation in total internal reflection occurs.

The surface plasmon sensor and the leaky mode sensor are sometimes used in random screening for finding an analyte combined with a predetermined ligand in the field of pharmacy or the like. In this case, the ligand is fixed on the film layer (the metal film in the case of the surface plasmon sensor, and the clad layer and the optical waveguide layer in the case of the leaky mode sensor), and buffers (sample liquid) containing therein various analytes are added to the ligand. Then the attenuation angle θsp is repeatedly measured each time a predetermined time lapses. When the analyte in the buffer is combined with the sensing material, the refractive index of the ligand changes with time due to combination with the analyte. Accordingly, by measuring the attenuation angle θsp, at which attenuation in total internal reflection takes place, for every predetermined time, thereby detecting whether the attenuation angle θsp changes, it is possible to know whether the analyte combines with the ligand or whether the analyte is a specific material to be combined with the ligand. As combinations of such an analyte and a ligand, there have been known combinations of antigens and an antibodies and of antibodies and other antibodies. For example, rabbit antihuman IgG antibody may be employed as the ligand with human IgG antibody employed as the analyte.

In order to detect the state of combination of the analyte in the buffer with the ligand, the total reflection attenuation angle θsp itself need not necessarily be detected. For example, a baseline is first measured by the use of a buffer containing no analyte, and then change of the attenuation angle θsp is measured when a buffer containing an analyte is added to the ligand, thereby measuring the state of combination of the analyte in the buffer with the ligand on the basis of the angle by which the attenuation angle θsp changes.

In the measuring system such as the surface plasmon resonance sensor, a method in which the measuring accuracy is improved on the basis of a reference method has been employed in order to cancel the measuring error due to external disturbance including a bulk effect due to the buffer, a temperature change of the ligand and/or the buffer or a change of the light source.

In the reference method, for instance, when the state of combination of the analyte with the ligand, two systems, one being a detecting system in which a ligand is fixed on the film layer and the other being a reference system in which no ligand is fixed on the film layer, are prepared. The result of detection of the detecting system is calibrated on the basis of the result of detection of the reference system, whereby the influence of the external disturbance is rejected. For instance, the result of detection of the reference system is subtracted from the result of detection of the detecting system.

However, it has been found that clear errors exist in the result of measurement even after calibration by the reference method. That is, there are some other factors of errors which cannot be calibrated by the reference method.

SUMMARY OF THE INVENTION

In view of the foregoing observations and description, the primary object of the present invention is to provide in a measuring method and a measuring system which generate evanescent waves by causing a light beam to be reflected in total internal reflection at an interface between a film layer in contact with a sample (an object to be measured) and a dielectric block and analyze the sample by measuring change of the intensity of the light beam reflected in total internal reflection at the interface a measuring method and a measuring system which are free from the problem described above.

We, these inventors, have ascertained that errors exist in the result of measurement even after calibration by the reference method. In order to investigate the cause thereof, we prepared two systems, one being a detecting system in which a ligand is fixed on the film layer and the other being a reference system in which no ligand is fixed on the film layer. We measured the change with time when a buffer containing therein an analyte is supplied to each of the systems after a reference buffer is supplied.

The result of the measurement is reported in FIGS. 11A and 11B. FIG. 11A is a graph showing an estimated result of the measurement, and FIG. 11B is a graph showing the actual result of the measurement. In FIGS. 11A and 11B, the ordinate shows an SPR signal and the abscissa shows a time.

When the measurement is done, as shown FIG. 11A, during the period from the time the reference buffer is supplied to the time the buffer containing therein an analyte is supplied (the reference period), the SPR signal should show the reference value (0RU) in each of the systems, for a while after the buffer containing therein an analyte is supplied (the reaction period), gradually change in the detecting system due to combination of the ligand and the analyte whereas though once slightly change due to the bulk effect of the buffer containing therein an analyte and be soon fixed to a constant value in the reference system, and during the period thereafter (the stabilized period), be kept unchanged at the value at which it is saturated during the reaction period in the detecting system whereas be kept unchanged at which it reaches during the reaction period in the reference system. However, in the actual result of the measurement, as shown in FIG. 11B, the SPR signal include drift components superimposed thereon different from each other in the detecting system and the reference system though approximately shows a tendency described above.

As the reason why the drift components are generated, various factors such as change of the temperature in the measuring system can be conceived. When the drift components are the same in the detecting system and the reference system, the drift components can be rejected by canceling the drift components of the systems by the reference method. However, when the drift components are different in the detecting system and the reference system, the drift components cannot be cancelled by the reference method and accordingly, accurate measuring result cannot be obtained.

From above, these inventors have revealed that the measuring error due to the drift components can be corrected by a following technique. The drift component is extracted from each of the result of measurement of the detecting system and that of the reference system. The result of measurement of the detecting system is calibrating on the basis of the result of measurement of the reference system by the reference method after removing the respective drift components from the result of measurement of the detecting system and that of the reference system. Or, the result of measurement of the detecting system is calibrated on the basis of the result of measurement of the reference system by the reference method and extracting and removing the drift components from the resulting result of measurement of the detecting system. The latter may be since the drift components linearly increases or decreases.

This invention has been made on the basis of the recognition. In accordance with the present invention, there is provided a first measuring method in a measuring method which makes measurement with a measuring system comprising a measuring unit having a dielectric block, a film layer formed on one face of the dielectric block and a sample holding mechanism for holding a sample in contact with the film layer with the film layer having a detecting area where a ligand is fixed to the surface thereof and a reference area where no ligand is fixed to the surface thereof, a light source emitting a light beam, an incident optical system which causes the light beam to impinge upon a first interface of the dielectric block and a detecting area of the film layer and a second interface of the dielectric block and a reference area of the film layer at various angles of incidence so that total internal reflection conditions are satisfied at the first and second interfaces, a photodetector means which detects the intensities of the light beams reflected in total internal reflection at the first and second interfaces independently from each other and a measuring means which measures information on refractive indexes of objects to be measured in contact with the pair of areas of the film layer on the basis of the result of detection of the photodetector means, which method comprises the steps of carrying out the measurement for a predetermined period in each of the detecting area and the reference area, calibrating the result of measurement in the detecting area on the basis of the result of measurement in the reference area, and removing from the result of measurement in the detecting area after the calibration drift components extracted from the result of measurement in the detecting area after the calibration by a predetermined method.

In accordance with the present invention, there is provided a second measuring method in a measuring method which makes measurement with a measuring system comprising a measuring unit having a dielectric block, a film layer formed on one face of the dielectric block and a sample holding mechanism for holding a sample in contact with the film layer with the film layer having a detecting area where a ligand is fixed to the surface thereof and a reference area where no ligand is fixed to the surface thereof, a light source emitting a light beam, an incident optical system which causes the light beam to impinge upon a first interface of the dielectric block and a detecting area of the film layer and a second interface of the dielectric block and a reference area of the film layer at various angles of incidence so that total internal reflection conditions are satisfied at the first and second interfaces, a photodetector means which detects the intensities of the light beams reflected in total internal reflection at the first and second interfaces independently from each other and a measuring means which measures information on refractive indexes of objects to be measured in contact with the pair of areas of the film layer on the basis of the result of detection of the photodetector means, which method comprises the steps of carrying out the measurement for a predetermined period of each of the detecting area and the reference area, correcting the result of measurement in the detecting area to remove from the result of measurement in the detecting area drift components extracted from the result of measurement in the detecting area by a predetermined method, correcting the result of measurement in the reference area to remove from the result of measurement in the reference area drift components extracted from the result of measurement in the reference area by a predetermined method, and calibrating the result of measurement in the detecting area after the correction on the basis of the result of measurement in the reference area after the correction.

In the first and second measuring methods, the predetermined method may be a method in which the rate of change with time of the difference between an estimated result of the measurement and the actual result of the measurement is calculated for a part of a predetermined period and the components which change at a rate of change calculated for the entire period of the predetermined period with a predetermined point in the predetermined period taken as a reference are taken as the drift components. The estimated result need not be limited to result estimated according to the form of the measurement but may be result represented by one of curves in a curve table prepared in advance to store various measuring patterns which is the closest to that representing the measuring signal (curve fitting).

In the second measuring method, either of "correcting the result of measurement in the detecting area to remove from the result of measurement in the detecting area drift components extracted from the result of measurement in the detecting area by a predetermined method" and "correcting the result of measurement in the reference area to remove from the result of measurement in the reference area drift components extracted from the result of measurement in the reference area by a predetermined method" may be performed first.

In accordance with the present invention, there is further provided a first measuring system in a measuring system comprising a measuring unit having a dielectric block, a film layer formed on one face of the dielectric block and a sample holding mechanism for holding a sample in contact with the film layer with the film layer having a detecting area where a ligand is fixed to the surface thereof and a reference area where no ligand is fixed to the surface thereof, a light source emitting a light beam, an incident optical system which causes the light beam to impinge upon a first interface of the dielectric block and a detecting area of the film layer and a second interface of the dielectric block and a reference area of the film layer at various angles of incidence so that total internal reflection conditions are satisfied at the first and second interfaces, a photodetector means which detects the intensities of the light beams reflected in total internal reflection at the first and second interfaces independently from each other and a measuring means which measures information on refractive indexes of objects to be measured in contact with the pair of areas of the film layer on the basis of the result of detection of the photodetector means, wherein the improvement comprises a calibrating means which calibrates the result of measurement in the detecting area carried out for a predetermined period on the basis of the result of measurement in the reference area carried out for a predetermined period, and a correcting means which removes from the result of measurement in the detecting area after the calibration drift components extracted from the result of measurement in the detecting area after the calibration by a predetermined method.

In accordance with the present invention, there is further provided a second measuring system in a measuring system comprising a measuring unit having a dielectric block, a film layer formed on one face of the dielectric block and a sample holding mechanism for holding a sample in contact with the film layer with the film layer having a detecting area where a ligand is fixed to the surface thereof and a reference area where no ligand is fixed to the surface thereof, a light source emitting a light beam, an incident optical system which causes the light beam to impinge upon a first interface of the dielectric block and a detecting area of the film layer and a second interface of the dielectric block and a reference area of the film layer at various angles of incidence so that total internal reflection conditions are satisfied at the first and second interfaces, a photodetector means which detects the intensities of the light beams reflected in total internal reflection at the first and second interfaces independently from each other and a measuring means which measures information on refractive indexes of objects to be measured in contact with the pair of areas of the film layer on the basis of the result of detection of the photodetector means, wherein the improvement comprises a correcting means which corrects the result of measurement in the detecting area to remove from the result of measurement in the detecting area drift components extracted from the result of measurement in the detecting area carried out for a predetermined period by a predetermined method and corrects the result of measurement in the reference area to remove from the result of measurement in the reference area drift components extracted from the result of measurement in the reference area carried out for a predetermined period by a predetermined method, and a calibrating means which calibrates the result of measurement in the detecting area corrected by the correcting means on the basis of the result of measurement in the reference area corrected by the correcting means.

In the first and second measuring systems, the predetermined method may be a method in which the rate of change with time of the difference between an estimated result of the measurement and the actual result of the measurement is calculated for a part of a predetermined period and the components which change at a rate of change calculated for the entire period of the predetermined period with a predetermined point in the predetermined period taken as a reference are taken as the drift components. The estimated result need not be limited to result estimated according to the form of the measurement but may be result represented by one of curve tables prepared in advance to store various measuring patterns which is the closest to that representing the measuring signal (curve fitting).

The measuring system in the measuring method of the present invention and the measuring system of the present invention may be a surface plasmon resonance sensor which measures on the basis of the surface plasmon resonance effect with the film layer of metal film or a leaky mode sensor which measures on the basis of the effect of excitation of the waveguide mode on an optical waveguide layer with the film layer formed of a clad layer which is formed on one face of the dielectric block and an optical waveguide layer which is formed on the clad layer.

The method of measuring the state on the film layer may be a method in which the attenuation angle or change of the attenuation angle is obtained by causing the light beam to impinge upon the interface between the dielectric block and the film layer at various angles and by detecting the light beam reflected at the same or a method in which the attenuation angle or change of the attenuation angle is obtained by causing light beams of different wavelengths to impinge upon the interface at various angles of incidence so that total internal reflection conditions are satisfied at the interface and detecting the intensity of the light beam reflected at the interface by the wavelengths thereby obtaining the degree of the attenuation of the intensity of light reflected in total internal reflection from the interface by the wavelengths as disclosed in "Porous Gold in Surface Plasmon Resonance Measurement" by D. V. Noort, et al., EUROSENSORS XIII, 1999, pp. 585-588.

Further, in the measuring system described above, the "information on the refractive index of the object to be measured" may be any so long as it changes with the refractive index of the object to be measured. For example, it may be on an attenuation angle which changes with the refractive index of the object to be measured, a wavelength of the light beam which generates attenuation in total internal reflection, change of the attenuation angle, change of the wavelength of the light beam which generates attenuation in total internal reflection.

In accordance with the first measuring method and the first measuring system of the present invention, since the error due to the drift components which cannot be calibrated by the reference method is corrected by carrying out the measurement for a predetermined period in each of the detecting area and the reference area, calibrating the result of measurement in the detecting area on the basis of the result of measurement in the reference area by the reference method, and removing from the result of measurement in the detecting area after the calibration drift components extracted from the result of measurement in the detecting area after the calibration by a predetermined method, the measuring accuracy of the measuring system can be improved.

In accordance with the second measuring method and the second measuring system of the present invention, since the error due to the drift components which cannot be calibrated by the reference method is corrected by carrying out the measurement for a predetermined period in each of the detecting area and the reference area, correcting the result of measurement in the detecting area to remove from the result of measurement in the detecting area drift components extracted from the result of measurement in the detecting area by a predetermined method, correcting the result of measurement in the reference area to remove from the result of measurement in the reference area drift components extracted from the result of measurement in the reference area by a predetermined method, and calibrating the result of measurement in the detecting area after the correction on the basis of the result of measurement in the reference area after the correction, the measuring accuracy of the measuring system can be improved.

DESCRIPTION OF THE PREFERRED EMBODIMENTS

Figure 1:
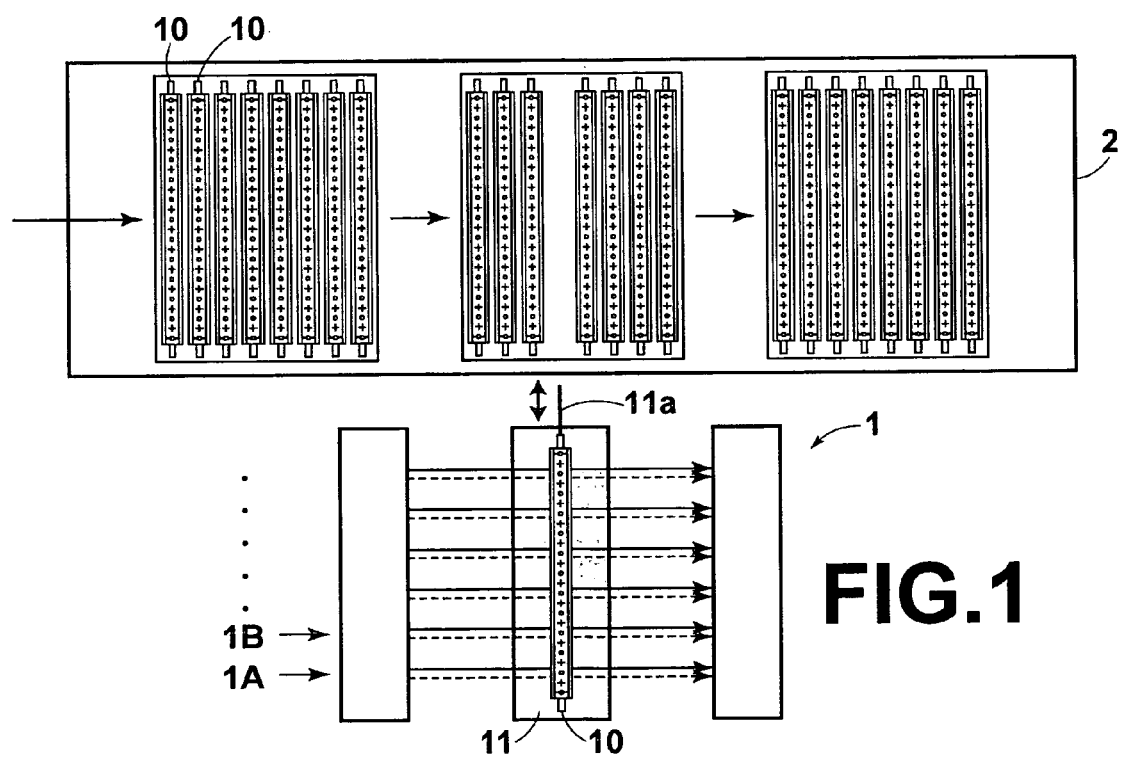
FIG. 1 is a plan view of a surface plasmon resonance sensor in accordance with a first embodiment of the present invention.

A measuring system in accordance with a first embodiment of the present invention is a surface plasmon resonance sensor which can analyze a plurality of samples at one time by causing light beams to impinge upon a plurality of measuring portions in parallel. FIG. 1 is a plan view of a surface plasmon resonance sensor in accordance with an embodiment of the present invention, FIG. 2 is a plan view of the measuring system of the surface plasmon resonance sensor, FIG. 3 is a side view of the measuring system of the surface plasmon resonance sensor, and FIG. 8 is a cross-sectional view taken along line VIII-VIII in FIG. 2.

The surface plasmon resonance sensor 1 of this embodiment is, as shown in FIG. 1, a surface plasmon resonance sensor which can analyze a plurality of samples at one time by causing light beams to impinge upon in parallel a plurality of measuring portions. The plurality of measuring portions are each formed in measuring units 10 and comprises a plurality of measuring systems 1A, 1B . . . substantially the same in structure. The arrangement of each of the measuring systems 1A, 1B . . . will be described hereinbelow with suffixes A, B . . . abbreviated.

Figure 2:
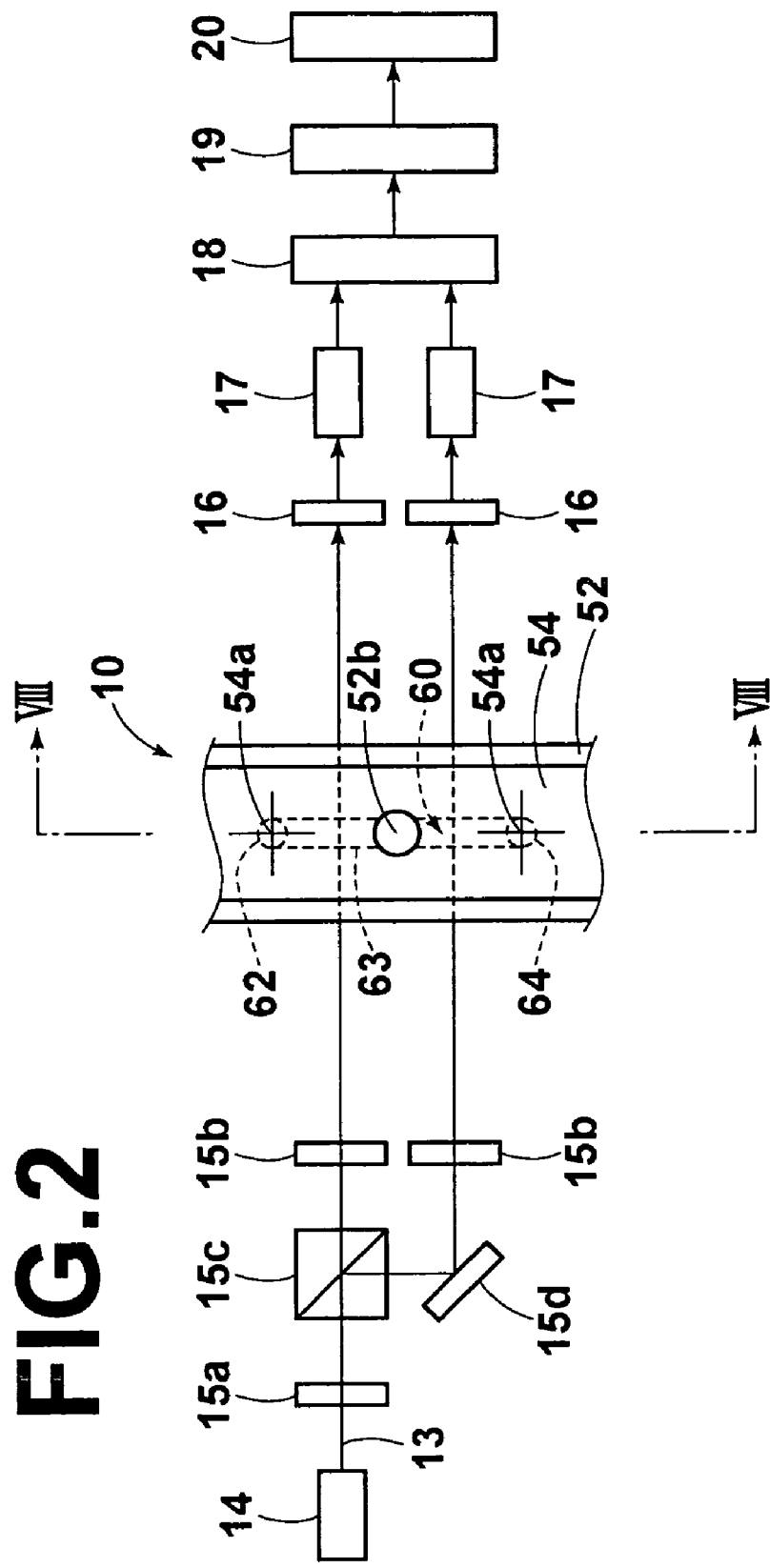
FIG. 2 is a plan view of the measuring system of the surface plasmon resonance sensor.
Figure 3:
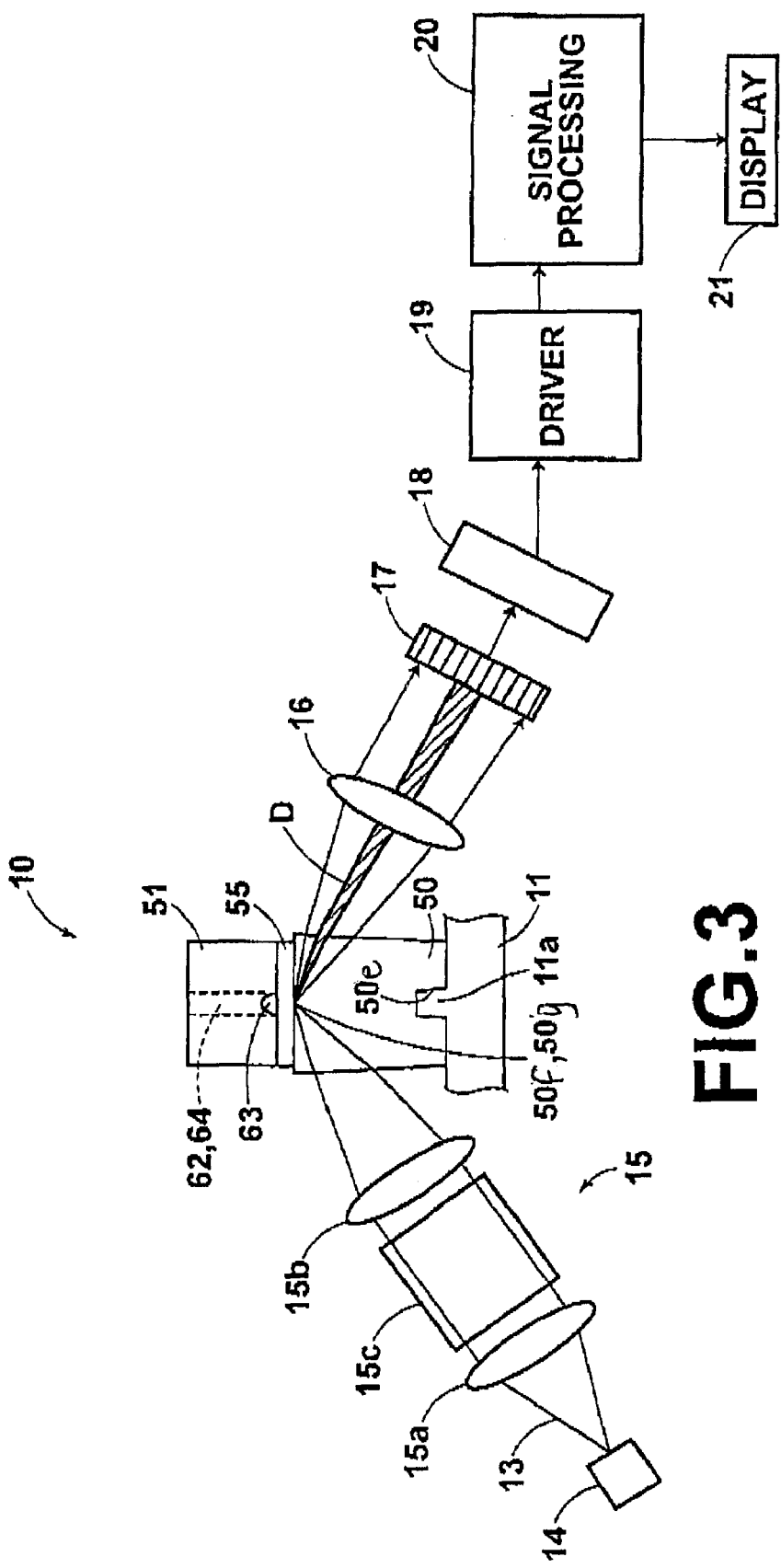
FIG. 3 is a side view of the measuring system of the surface plasmon resonance sensor.
Figure 8:
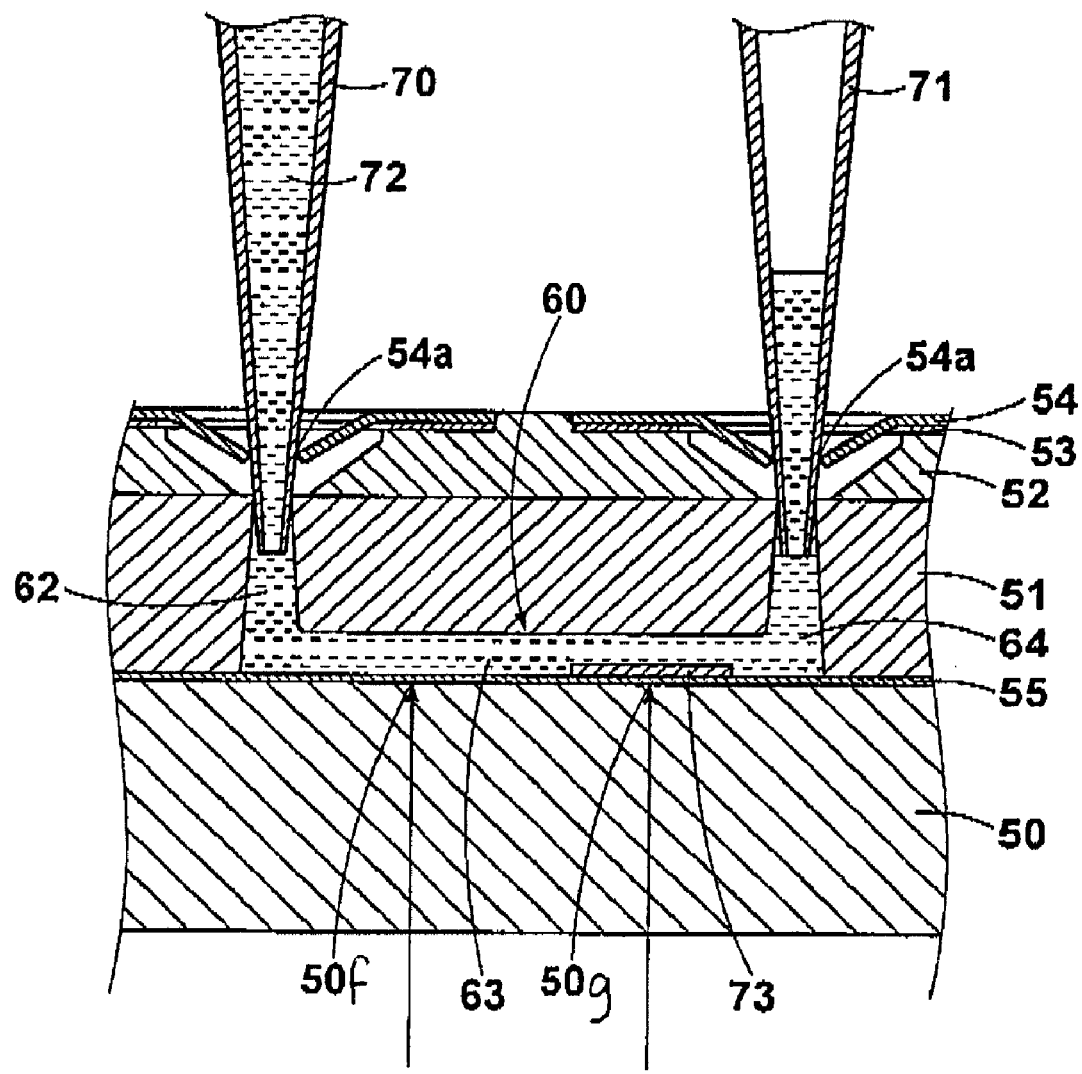
FIG. 8 is a cross-sectional view taken along line VIII-VIII in FIG. 2.

As shown in FIGS. 2, 3 and 8, each measuring system comprises a light source 14 formed, for instance, by a semiconductor laser generating a light beam 13 (will be referred to as "laser 14", hereinbelow). An incident optical system 15 causes the light beams 13 to enter the measuring unit 10 in parallel to impinge upon interfaces 50f and 50g between a dielectric block 50 and metal film 55 (which are positioned below the flow passage 60, i.e., measuring portion) at various angles of incidence. A pair of collimator lenses 16 respectively collimate the light beams 13 reflected at the respective interfaces 50f and 50g. A pair of photodiode arrays 17 respectively detect the collimated light beams 13. A differential amplifier array 18 is connected to the photodiode arrays 17. A driver 19 is provided. A signal processing portion 20 which may be, for instance, a computer system is provided. A display portion 21 is connected to the signal processing portion 20. The signal processing portion 20 functions as a calibrating means which calibrates result of measurement by the reference method and a correcting means which carries out correction where drift components are removed from the result of measurement. Processing by the calibrating means and the correcting means will be described in detail later.

Figure 4:
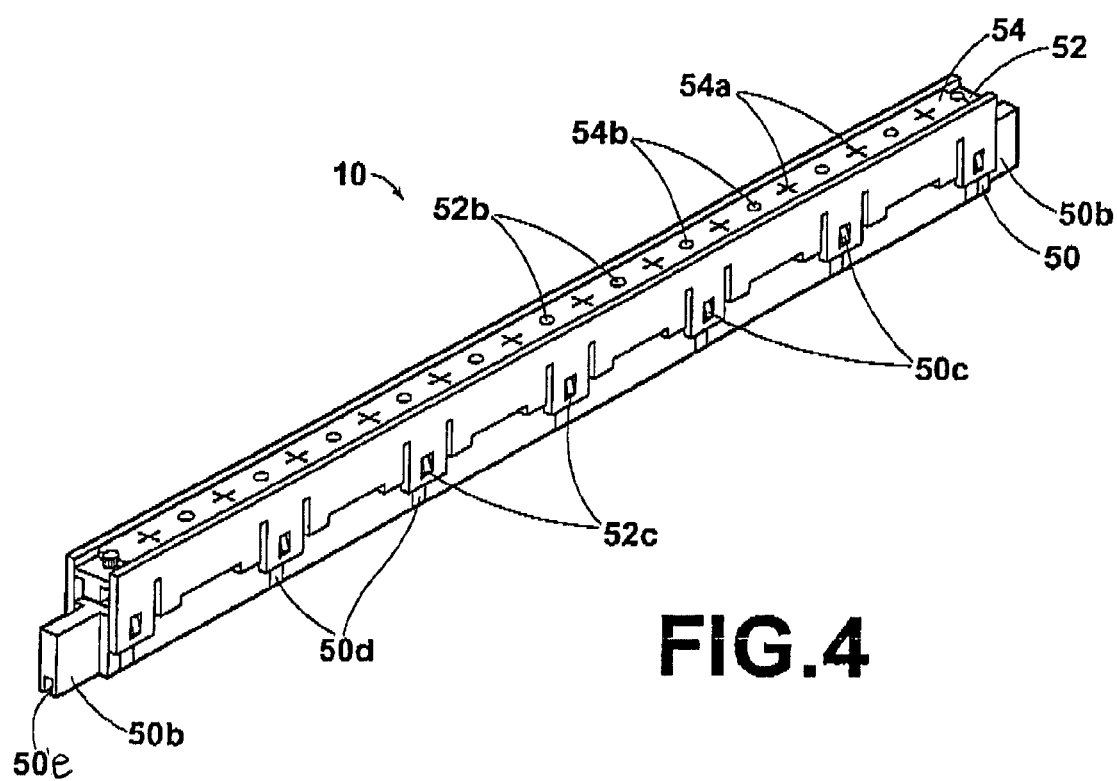
FIG. 4 is a perspective view of the measuring unit of the surface plasmon resonance sensor.
Figure 5:
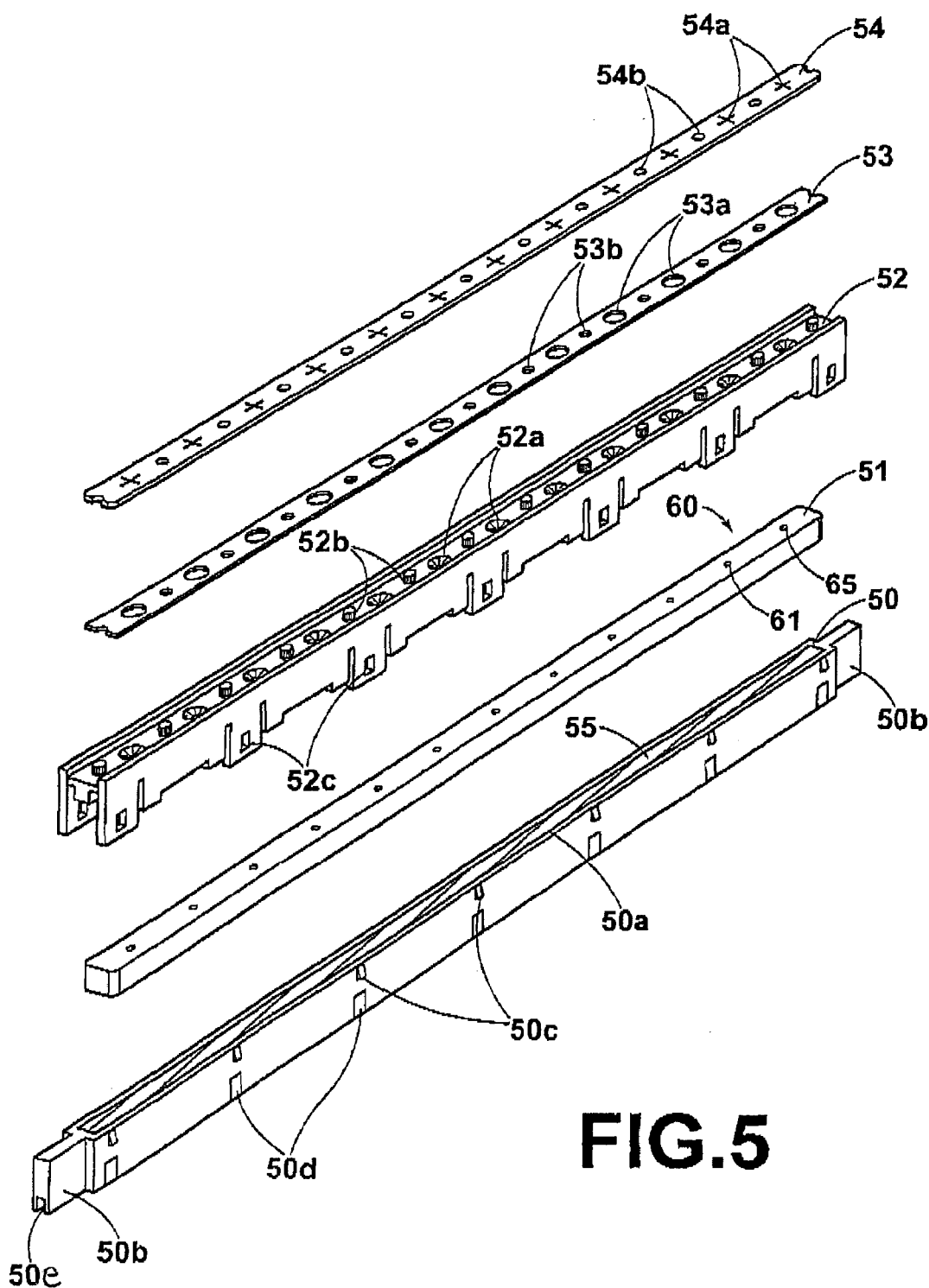
FIG. 5 is an exploded perspective view of the measuring unit.
Figure 6:
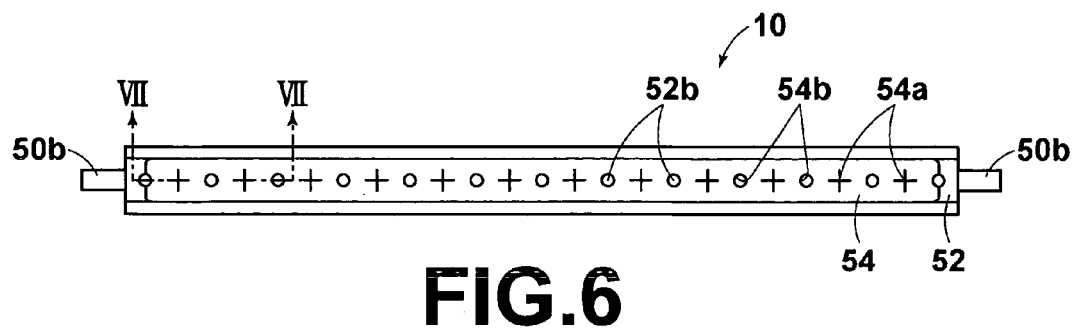
FIG. 6 is a plan view of the measuring unit.
Figure 7:
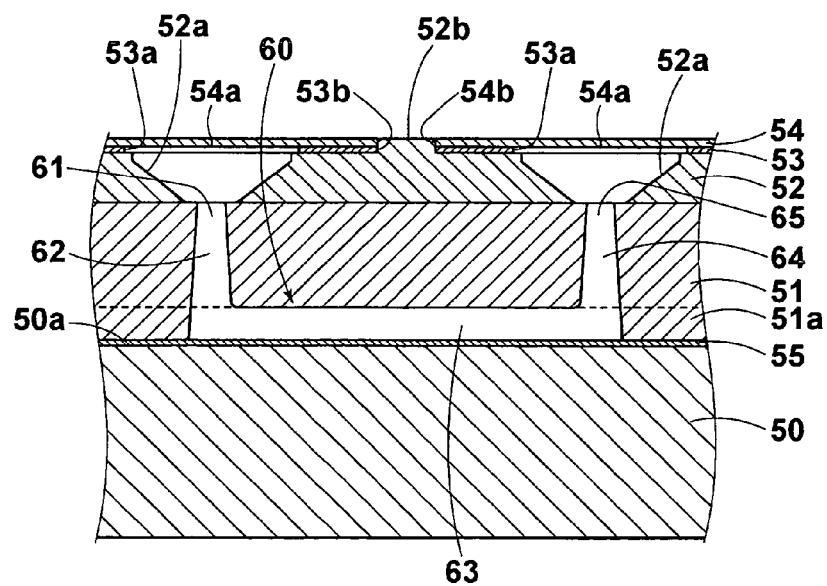
FIG. 7 is a cross-sectional view taken along line VII-VII in FIG. 6.

The measuring unit 10 will be described first. FIG. 4 is a perspective view of the measuring unit 10, FIG. 5 is an exploded perspective view of the measuring unit 10, FIG. 6 is a plan view of the measuring unit 10, and FIG. 7 is a cross-sectional view taken along line VII-VII in FIG. 6.

The measuring unit 10 comprises the dielectric block 50 which is transparent to the light beam and has a flat and smooth upper surface 50a on which the metal film layer 55 is formed. A flow passage member 51 is held in close contact with the metal film layer 55. A holding member 52 is engaged with the dielectric block 50 to hold the flow passage member 51 on the upper surface 50a of the dielectric block 50.

The dielectric block 50 is formed, for instance, by transparent resin and has a body shaped like a trapezoid where the lower side is shorter than the upper side in a cross-section perpendicular to the longitudinal direction. The dielectric block 50 is formed with a holding portion 50b on each end of the body and formed integrally with a prism portion which causes the light beam emitted from the light source of a measuring system to be described later to impinge upon the interface of the dielectric block 50 and the metal film 55 and causes the light beam reflected at the interface in total internal reflection to emit toward the photodetector means of the measuring system. The holding portion 50b of the dielectric block 50 is thinner than the body of the dielectric block 50 as seen from above or from below. Engagement projections 50c which are to be engaged with an engagement hole 52c on the holding member 52 (to be described later) and perpendicular projections 50d which are perpendicular in their side surfaces are formed on the longitudinal side surfaces of the body of the dielectric block 50 to be opposed to each other on each side surfaces of the body of the dielectric block 50. A sliding groove 50e is formed on the bottom of the body of the dielectric block 50 to extend in parallel to the longitudinal direction thereof.

In the flow passage member 51, a plurality of flow passages 60, each comprising a supply passage 62 from an inlet 61 to a measuring portion 63 and a discharge passage 64 from the measuring portion 63 to an outlet 65, are formed and linearly arranged in the longitudinal direction of the flow passage member 51.

As shown in FIG. 7, the outlet of the supply passage 62 and the inlet of the discharge passage 64 open in a lower portion of the flow passage member 51, and a seal portion 51a circumscribing the outlet of the supply passage 62 and the inlet of the discharge passage 64 is formed in an area of the flow passage member 51 which is positioned in the bottom surface of the flow passage member 51 and is brought into contact with the surface of the metal film 55. The inner side of the seal portion 51a forms the measuring portion 63. Accordingly, when the flow passage member 51 is held in close contact with the metal film 55 on the dielectric block 50, the measuring portion 63 in the seal portion 51a comes to function as a flow passage. The seal portion 51a may be formed integrally with an upper portion of the flow passage member 51 or may be formed by a material different from the upper portion of the flow passage member 51 and may be subsequently attached to the upper portion of the flow passage member 51. For example, the seal portion 51a may be an O-ring attached to the upper portion of the flow passage member 51.

In a measuring system such as a surface plasmon resonance sensor employing the measuring unit of this embodiment, a liquid sample containing therein protein is used is expected. Since it is difficult to effect an accurate measurement when protein in the liquid sample is solidified in the flow passage 60, it is preferred that the flow passage member 51 be formed by a material which does not exhibit non-specific adsorption to proteins. For example, it is preferred that the flow passage member 51 is formed by silicone or polypropylene. Further, by forming the flow passage member 51 by an elastic material, the flow passage member 51 can be surely held in close contact with the metal film 55 and the leakage of the liquid sample through the contact surface can be prevented.

The holding member 52 is formed of an elastic material such as polypropylene and is substantially U-shaped in cross-section transverse to the longitudinal direction thereof and is formed in a position opposed to the inlet 61 or the outlet 65 of the flow passage member 51 in the upper plate (the holding plate portion) thereof with tapered pipette insertion holes 52a which taper toward the flow passage member 51. Locator bosses 52b are formed in the upper surface of the holding member 52 between the pipette insertion holes 52a and outside the pipette insertion holes 52a at the ends of the row of the pipette insertion holes 52a.

Further, an evaporation preventing member 54 is applied to the upper surface of the holding member 52 with double-coated tape (adhesive member) 53. As shown in FIG. 5, the double-coated tape 53 is provided with holes 53a and 53b respectively in positions opposed to the pipette insertion holes 52a and the locator bosses 52b. Similarly, the evaporation preventing member 54 is provided with slits 54a and holes 54b respectively in positions opposed to the pipette insertion holes 52a and the locator bosses 52b. With the locator bosses 52b inserted in the holes 53b of the double-coated tape 53 and the holes 54b of the evaporation preventing member 54, the evaporation preventing member 54 is applied to the upper surface of the holding member 52, whereby the slits 54a of the evaporation preventing member 54 are opposed to the inlets 61 and the outlets 65 of the flow passage member 51. It is necessary to form the evaporation preventing member 54 by an elastic material so that a pipette can be inserted through the silts 54a and the evaporation preventing member 54 is formed, for instance, by silicone or polypropylene. The holding member 52 and the evaporation preventing member 54 may be formed integrally with each other and in addition, the flow passage member 51 may be formed integrally with the holding member 52 and the evaporation preventing member 54.

The engagement holes 52c are adapted to be engaged with the engagement projections 50c of the dielectric block 50 and are formed in the longitudinal side plates of the holding member 52. The holding member 52 is mounted on the dielectric block 50 with the engagement holes 52c engaged with the engagement projections 50c so that the flow passage member 51 is sandwiched between the holding member 52 and the dielectric block 50 and held on the upper surface 50a of the dielectric block 50.

As shown in FIG. 7, in a state where the flow passage member 51 is sandwiched between the holding member 52 and the dielectric block 50, the inlets 61 and the outlets 65 of the flow passage member 51 are isolated from the atmosphere by the evaporation preventing member 54 and the liquid sample injected into the flow passage 60 is prevented from evaporating.

The incident optical system 15 comprises a collimator lens 15a which collimates the light beam 13 emitted from the laser 14 as a divergent light beam. A half-silvered mirror 15c splits the collimated light beam 13 into two light beams 13. A mirror 15d reflects toward the measuring unit 10 the light beam 13 reflected by the half-silvered mirror 15c. A pair of condenser lenses 15b converge the light beam 13 passing through the half-silvered mirror 15c and the light beam 13 reflected by the mirror 15d on the interfaces 50f and 50g.

Since converged as described above, the light beams 13 include components impinging upon the interfaces 50f and 50g at various angles of incidence θ. The angles of incidence θ are all not smaller than the angle of total internal reflection. Accordingly, the light beams 13 are reflected in total internal reflection at the interfaces 50f and 50g and the reflected light beams 13 include components reflected at the interfaces 50f and 50g at various angles of reflection. The incident optical system 15 may be arranged to cause the light beams 13 to impinge upon the interfaces 50f and 50g in a defocused state. This arrangement averages errors in detecting states of surfaces plasmon resonance and improves measuring accuracy.

The light beams 13 are caused to impinge upon the corresponding interfaces 50f and 50g in a p-polarized state. This can be realized by positioning the laser 14 so that its direction of polarization is in the predetermined direction. Otherwise, the direction of polarization of the light beams 13 may be controlled by a wavelength plate.

In this embodiment, the light beams 13 impinge upon in parallel the two interfaces 50f and 50g of the measuring portion 63 of each flow passage 60 of the measuring unit 10 as shown in FIG. 8. Nothing is fixed to the metal film 55 on the interface 50f to form a reference area whereas a ligand 73 is fixed to the metal film 55 on the other interface 50g to form a detecting area so that result of detection can be calibrated by a reference method described later.

Analysis of the sample by the surface plasmon resonance sensor 1 will be described, hereinbelow. Prior to measurement, the measuring unit 10 is moved to a measuring position on a chip holding portion 11 from an incubator 2. In the chip holding portion 11, a rail 11a to be engaged with the sliding groove 50e of the dielectric block 50 so that high positional accuracy can be ensured when the measuring unit 10 is moved. After the measuring unit 10 is placed on the chip holding portion 11, the perpendicular projections 50d on the dielectric block 50 is sandwiched by a fixing mechanism (not shown), whereby the measuring unit 10 is fixed in the measuring position on the chip holding portion 11. Thereafter, as shown in FIG. 8, a pipette chip 70 for supplying a liquid sample is inserted into the inlet 61 of the flow passage member 51 and a pipette chip 71 for sucking a liquid sample is inserted into the outlet 65 of the same, thereby supplying a buffer containing an analyte or a reference buffer as a buffer 72 to the measuring portion 63 of the flow passage 60 from the pipette chip 70 for supplying a liquid sample. Then, the measurement is started.

As shown in FIG. 3, a light beam 13 emitted from the laser 14 as a divergent light beam is converged on the interfaces 50f and 50g between the metal film 55 and the dielectric block 50 by virtue of the optical system 15. Each of the light beams 13 include components impinging upon the interfaces 50f and 50g at various angles of incidence θ. The angles of incidence θ are all not smaller than the angle of total internal reflection. Accordingly, the light beams 13 are reflected in total internal reflection at the interfaces 50f and 50g and the reflected light beams 13 include components reflected at the interfaces 50f and 50g at various angles of reflection.

The two light beams 13 respectively collimated by collimator lenses 16 into parallel light beams after reflected in total internal reflection at the interfaces 50f and 50g are respectively detected by the pair of photodiode arrays 17. In this particular embodiment, each photodiode array 17 comprises a plurality of photodiodes 17a, 17b, 17c . . . which are arranged in a row in a direction substantially perpendicular to the direction, in a plane shown in FIG. 3, in which the collimated light beam 13 travels. That is, each components of the light beams 13 respectively reflected in total internal reflection at the interfaces 50f and 50g at various reflecting angles are received by different photodiodes.

Figure 9:
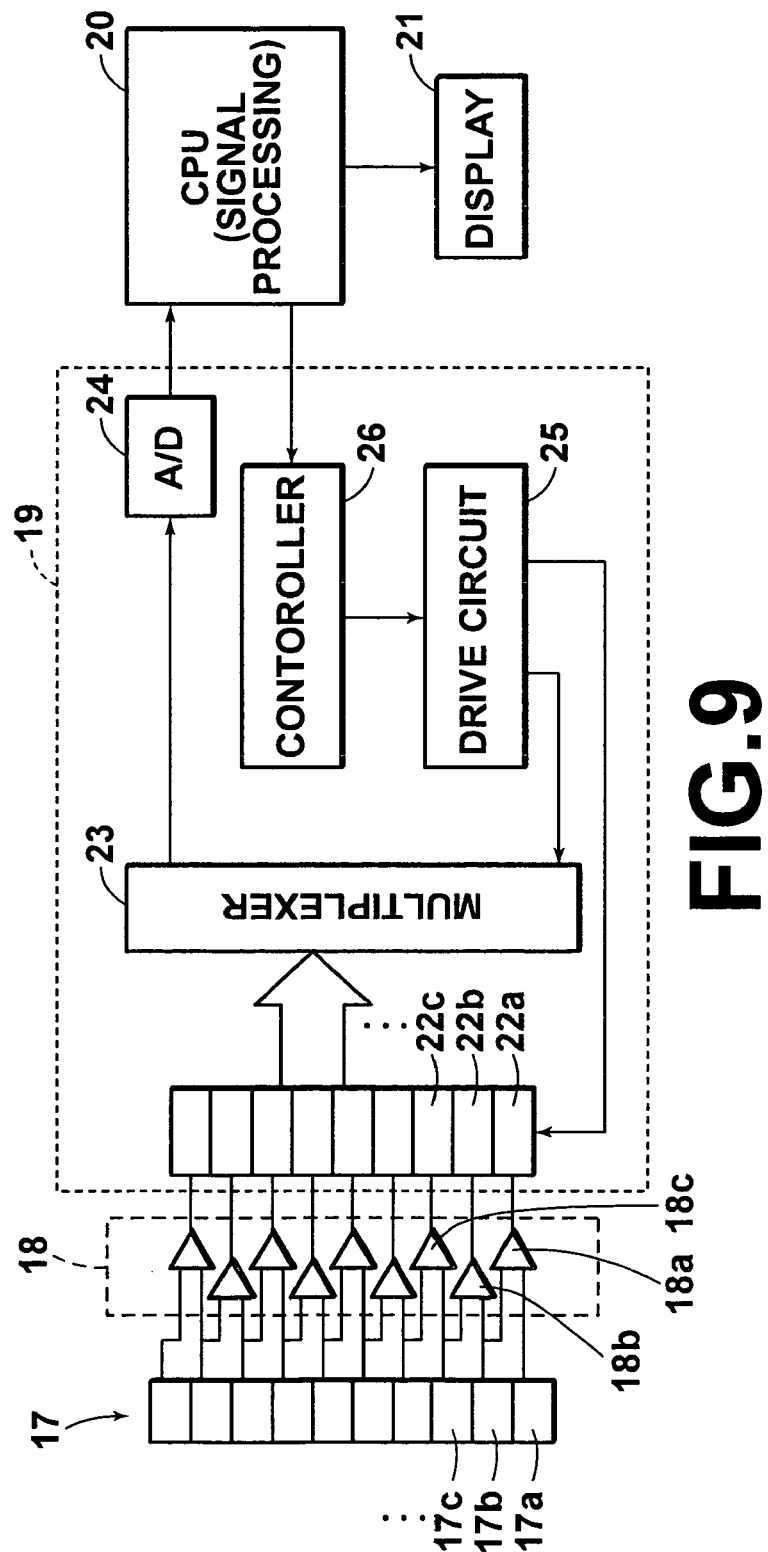
FIG. 9 is a block diagram showing an electric arrangement of the measuring system of the surface plasmon resonance sensor.

FIG. 9 is a block diagram showing an electric arrangement of the surface plasmon resonance sensor. As shown in FIG. 9, the driver 19 comprises sample hold circuits 22a, 22b, 22c . . . which hold the outputs of respective differential amplifiers 18a, 18b, 18c . . . of the differential amplifier array 18. The outputs of the sample hold circuits 22a, 22b, 22c . . . are input to a multiplexer 23. An A/D converter 24 which digitizes the output of the multiplexer 23 and inputs the digitized output of the multiplexer 23 into the signal processing portion 20. A driving circuit 25 drives the multiplexer 23 and the sample hold circuits 22a, 22b, 22c . . . . A controller 26 controls the driving circuit 25 under an instruction from the signal processing portion 20. The differential amplifier array 18, the driver 19 and the signal processing portion 20 execute the similar processes to the inputs from the pair of photodiode arrays 17.

Each of the outputs of the photodiodes 17a, 17b, 17c . . . is input into one of the differential amplifiers 18a, 18b, 18c . . . . At this time, outputs of adjacent two photodiodes are into one differential amplifier. Accordingly, the outputs of the respective differential amplifiers 18a, 18b, 18c . . . may be considered to be differentials of the light detecting signals output from the photodiodes 17a, 17b, 17c . . . in the direction in which the photodiodes 17a, 17b, 17c . . . are arranged.

The outputs of the differential amplifiers 18a, 18b, 18c . . . are held by the sample hold circuits 22a, 22b, 22c . . . at a predetermined timing and input into the multiplexer 23. The multiplexer 23 inputs the outputs of the differential amplifiers 18a, 18b, 18c . . . held by the sample hold circuits 22a, 22b, 22c . . . into the A/D converter 24 in a predetermined order. The A/D converter 24 digitizes the outputs and inputs the digitized outputs into the signal processing portion 20.

Figure 10A:
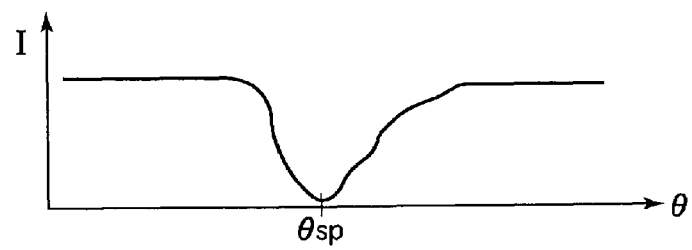
FIGS. 10A, 10B and 10C are graphs for illustrating the relation between the angle of incidence of light to the interface and the intensity of the reflected light beam detected in the measuring system of the surface plasmon resonance sensor, and the relation between the angle of incidence of light to the interface and the differentiation of the light intensity detecting signal.
Figure 10B:
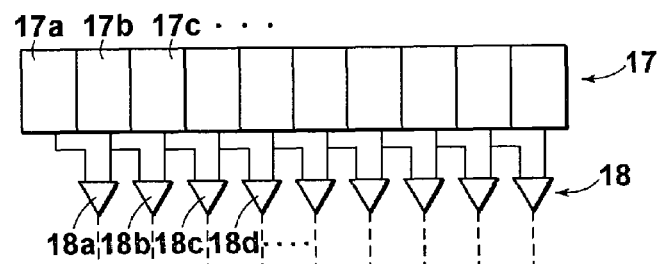
Figure 10C:
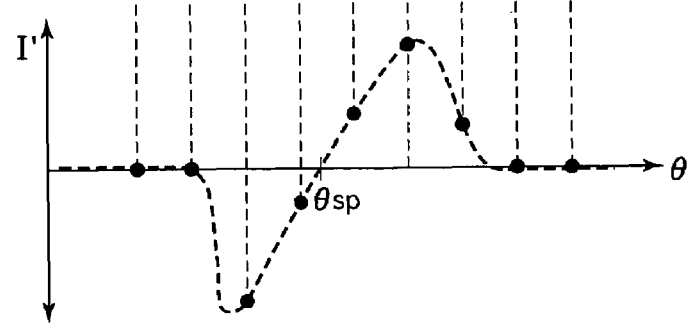

FIGS. 10A, 10B and 10C are views for illustrating the intensity of the light beam 13 reflected in total internal reflection at the interface 50f (or 50g) for each angle of incidence θ. The relation between the angle of incidence θ of the light beam 13 to the interface 50f (or 50g) and intensity I is as shown by the graph shown in FIG. 10A.

The component impinging upon the interface 50f (or 50g) at a particular angle of incidence θsp excites the surface plasmon at the interface between the metal film 55 and the buffer 72 and the intensity I of light reflected in total internal reflection sharply drops for this component. That is, the angle of incidence θsp is the attenuation angle and the intensity I is minimized at the angle θsp. The drop of the intensity I is observed as a dark line in the reflected light beams as denoted by D in FIG. 3.

FIG. 10B shows the direction in which the photodiodes 17a, 17b, 17c . . . are arranged. As described above, the positions of the photodiodes 17a, 17b, 17c . . . correspond to the angles of incidence θ in the direction in which the photodiodes 17a, 17b, 17c . . . are arranged.

The relation between the positions of the photodiodes 17a, 17b, 17c . . . in the direction in which the photodiodes 17a, 17b, 17c . . . are arranged, that is, the angles of incidence θ and the outputs I' of the differential amplifiers 18a, 18b, 18c . . . (differentials of the intensity I) is as shown on FIG. 10C.

The signal processing portion 20 selects a differential amplifier out of the differential amplifiers 18a, 18b, 18c . . . whose output is the closest to the differential I' for the attenuation angle θsp (I'=0) on the basis of the differentials I' input from the A/D converter 24 (amplifier 18d in this particular example), and causes the display portion 21 to display the value after a predetermined correction. When there is a differential amplifier which outputs 0 (differential I'=0), it is needless to say that the signal processing portion 20 selects the differential amplifier in such a case.

Thereafter, each time a predetermined time lapses, the differential I' output from the selected differential amplifier 18d is displayed by the display portion 21 after the predetermined correction. The differential I' becomes larger or smaller as the dielectric constant or the refractive index of the material in contact with the film 55 of the measuring chip changes and the attenuation angle θsp changes so that the curve shown in FIG. 10A moves left and right. Accordingly, by measuring the differential I' continuously with lapse of time, the change of the refractive index of the buffer 72 (or the ligand 73) in contact with the metal film 55 can be detected.

Especially, in this embodiment, since the refractive index of the ligand 73 changes with combination of the ligand 73 and the analyte when the analyte in the buffer 72 is the specific material which is combined with the ligand 73, whether the analyte is the specific material which is combined with the ligand 73 can be detected by continuously measuring the differential I'.

Further, in this embodiment, since the metal film 55 has a detecting area and a reference area and a reference measurement and a measurement of combination are simultaneously effected, the result of measurement calibrated on the basis of measuring errors due to deformation of the ligand 73 can be further calibrated on the basis of measuring errors due to external disturbance, for instance, the change of the temperature of the buffer 72 or fluctuation of the light source, by the reference method.

Figure 11A:
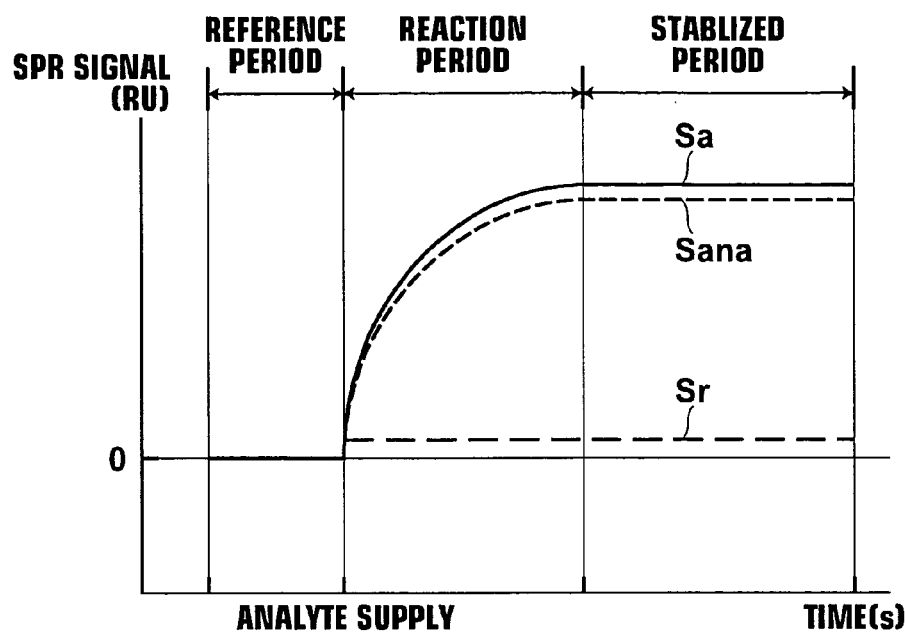
FIG. 11A is a graph showing an estimated result of measurement when the change with time is measured with a buffer containing therein analyte is supplied to each of the systems of the detecting area and the reference area after a reference buffer is supplied to the system.
Figure 11B:
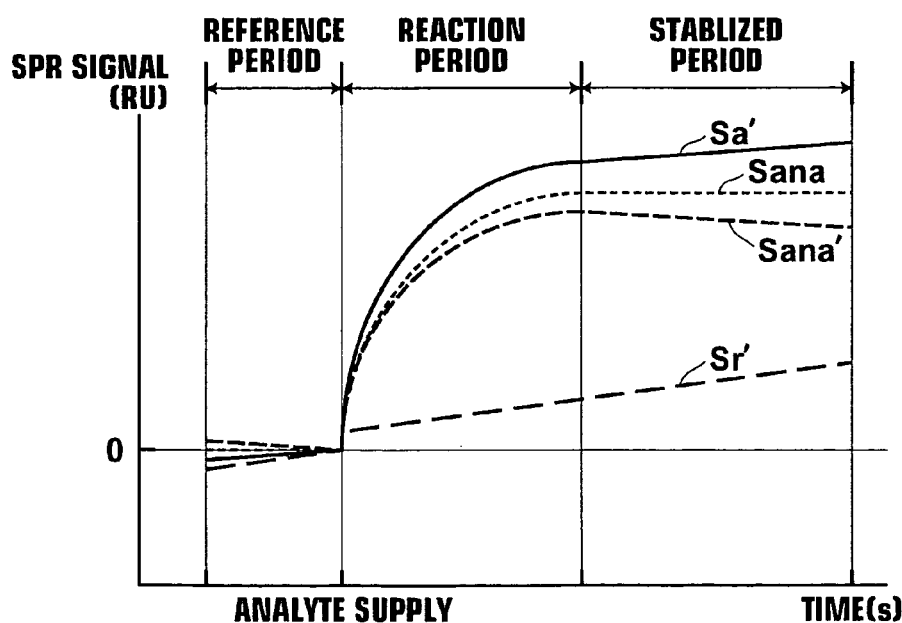
FIG. 11B is a graph showing the actual result of measuring when the change with time is measured with a buffer containing therein analyte is supplied to each of the systems of the detecting area and the reference area after a reference buffer is supplied to the system.

The result of the measurement (as an example of the measurement described above) when the change with time when a buffer containing therein an analyte was supplied to each of the systems after a reference buffer was supplied is reported in FIGS. 11A and 11B. FIG. 11A is a graph showing an estimated result of the measurement, and FIG. 11B is a graph showing the actual result of the measurement. In FIGS. 11A and 11B, the ordinate shows an SPR signal and the abscissa shows a time.

When the measurement is done, as shown FIG. 11A, the measuring signal Sa of the detecting area should show the reference value (ORU) during the period from the time the reference buffer is supplied to the time the buffer containing therein an analyte is supplied (the reference period), and gradually change due to combination of the ligand and the analyte for a while after the buffer containing therein an analyte is supplied (the reaction period), and be kept unchanged at which it is saturated during the reaction period during the period thereafter (the stabilized period), while the measuring signal Sr of the reference area should show the reference value (ORU) during the reference period, and be soon fixed to a constant value though once slightly change due to the bulk effect of the buffer containing therein an analyte and, be kept unchanged at the value at which it reaches during the reaction period in the stabilized period. Accordingly, when the measuring signal Sa of the detecting area is calibrated on the basis of the measuring signal Sr of the reference area by the reference method, a signal Sana shown in FIG. 11A should be obtained.

However, in the actual result of the measurement, as shown in FIG. 11B, though a tendency described above is approximately shown, drift components different from each other are superimposed on the measuring signal Sa' in the detecting area and the measuring signal Sr' in the reference area, and when the measuring signal Sa' of the detecting area is calibrated on the basis of the measuring signal Sr' of the reference area by the reference method, a signal Sana' shown in FIG. 11B, which differs from the estimated measuring signal Sana, is obtained.

Figure 12:
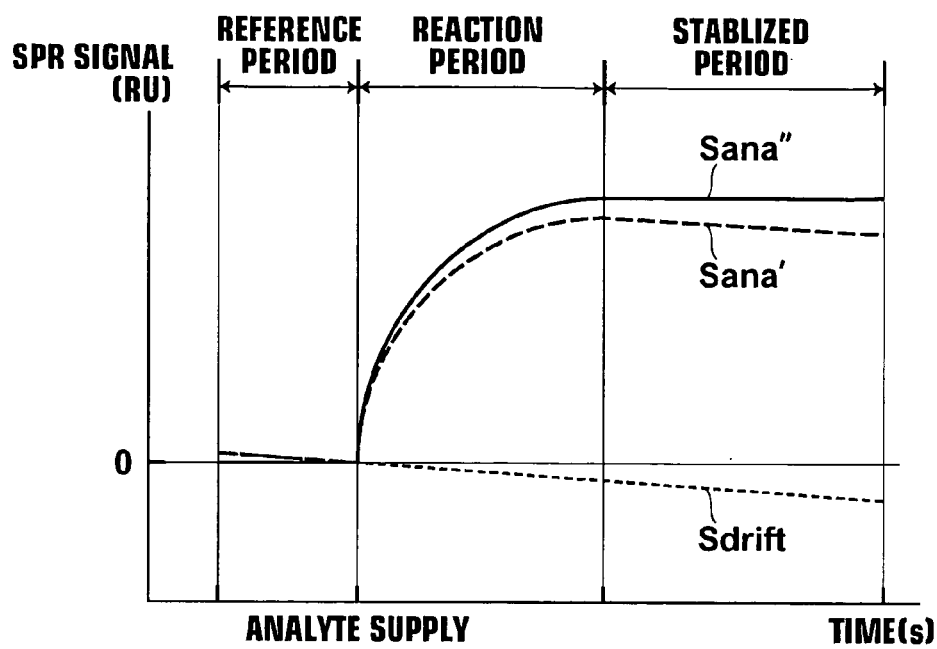
FIG. 12 is a graph showing a method of correction when the change with time is measured with a buffer containing therein analyte is supplied to each of the systems of the detecting area and the reference area after a reference buffer is supplied to the system.

In this embodiment, as shown in FIG. 12, in the reference period (may be the stabilized period) during which the measuring signal Sana' is estimated to be constant, the rate of change with time of the difference between the measuring signal Sana' and the estimated result (ORU constant) is calculated and the components which change at the rate of change with time which has been calculated for the entire period of the measuring period with the instance when a buffer containing therein analyte is supplied (the border between the reference period and the reaction period) taken as a reference are taken as drift components Sdrift. Then by correcting the measuring signal Sana' to remove the drift components Sdrift therefrom, a measuring signal Sana" substantially equal to the estimated signal Sana can be obtained. As a method of removing the drift components Sdrift from the measuring signal Sana', there is a method where a difference between the drift components Sdrift and the measuring signal Sana' is obtained. However, it need not be limited to the method.

Since the error due to the drift components which cannot be calibrated by the reference method can be corrected by the embodiment described above, the measuring accuracy of the measuring system can be improved.

Figure 13:
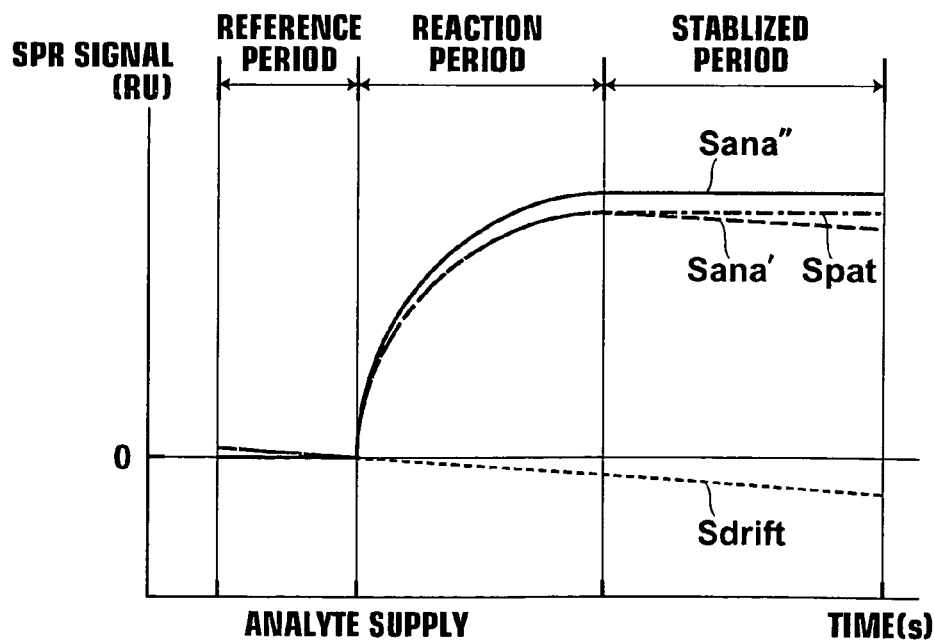
FIG. 13 is a graph showing another method of correction when the change with time is measured with a buffer containing therein analyte is supplied to each of the systems of the detecting area and the reference area after a reference buffer is supplied to the system.

Otherwise, the drift components Sdrift may be calculated by preparing in advance a curve table storing various measuring patterns as shown in FIG. 13 and by extracting a curve (Spat) therefrom which is the closest to that representing the measuring signal Sana' (curve fitting), thereby calculating the drift components Sdrift on the basis of the difference between the curve Spat and the measuring signal Sana'.

Though, in this embodiment, nothing is fixed to the reference area on the metal film 55, it is preferred that the reference area does not react the analyte in the buffer 72. For this purpose, for instance, alkylthiol, aminoalcohol, or aminoether may be fixed to the metal film 55. Otherwise, organic film which cannot fix the ligand or protein which is known not to react with the analyte to be used in the measurement may be used as the reference surface.

Further, the measuring system need not be limited to those where the measurements on all the flow passages formed in the measuring unit are simultaneously effected by a plurality of surface plasmon measuring systems but may be provided with a single surface plasmon measuring system so that a plurality of flow passages formed by a measuring unit are measured in sequence by moving the measuring unit relatively to the measuring system.

Figure 14:
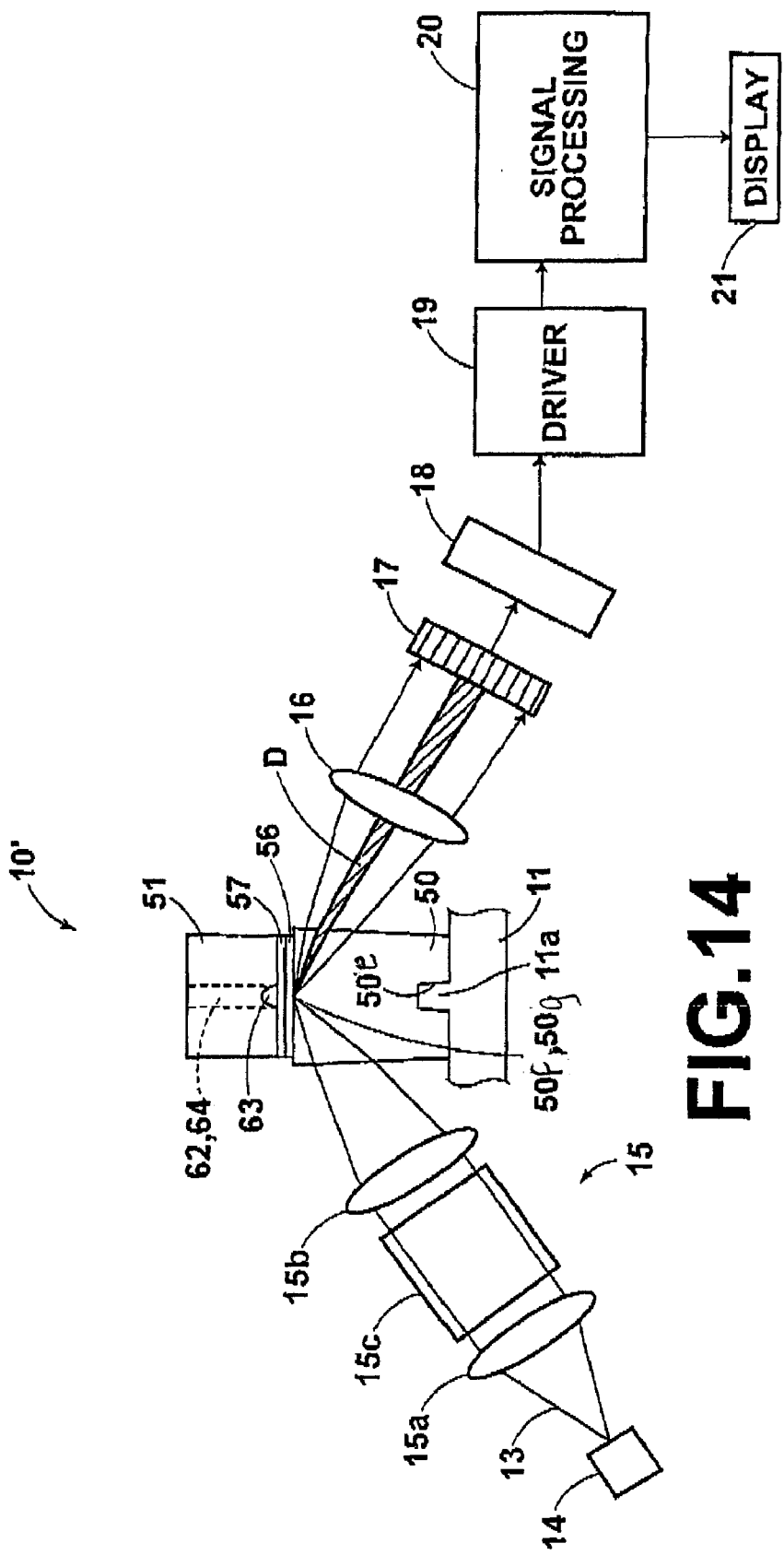
FIG. 14 is a side view of the measuring system of a leaky mode sensor in accordance with a second embodiment of the present invention.

A measuring unit in accordance with a second embodiment of the present invention will be described with reference to FIG. 14, hereinbelow. In FIG. 14, elements analogous to those shown in FIG. 3 are given the same reference numerals and will not be described here unless necessary. The measuring unit of the second embodiment is used for a leaky mode sensor and the same in the measuring system as the surface plasmon resonance sensor of the first embodiment.

This measuring unit 10' comprises a clad layer 56 and a waveguide layer 57 which are laminated on this order on one surface (an upper surface in the illustrated embodiment) of the dielectric block 50. The dielectric block 50 is formed by synthetic resin, optical glass of BK7, or the like. The clad layer 56 is formed into film by a dielectric material or a metal such as gold which is lower in refractive index than the dielectric block 50 and the waveguide layer 57 is formed into film by a dielectric material such as PMMA which is higher in refractive index than the clad layer 56. The clad layer 56 is 36.5 nm in thickness when formed by metal film, and the waveguide layer 57 is 700 nm in thickness when formed by PMMA.

In the leaky mode sensor with this arrangement, when the light beam 13 emitted from the laser 14 is caused to impinge upon the clad layer 56 through the dielectric block 50 at an angle not smaller than an angle of total internal reflection, the light beam 13 is reflected in total internal reflection at the interface 50f or 50g between the dielectric block 50 and the clad layer 56. However, light having a particular wave number and impinging upon the optical waveguide layer 57 at a particular angle of incidence comes to propagate through the optical waveguide layer 57 in a waveguide mode after passing through the clad layer 56. When the waveguide mode is thus excited, almost all the incident light is taken in the optical waveguide layer and accordingly, the intensity of light reflected in total internal reflection at the interface 50f or 50g sharply drops. That is, attenuation in total internal reflection occurs.

Since the wave number of light to be propagated through the optical waveguide layer 57 in a waveguide mode depends upon the refractive index of the buffer 72 or the ligand 73 on the optical waveguide layer 57, the refractive index of the buffer 72 or the ligand 73 can be detected on the basis of the angle of incidence θsp at which the attenuation in total internal reflection occurs. Change of the combination of the ligand 73 and the analyte to be measured in the buffer 72 can detected on the basis of the differentials I' output by the respective differential amplifiers of the differential amplifier array 18.

With this embodiment, result similar to that obtained by the first embodiment can be obtained.

Though, in the embodiments described above, the result of measurement in the detecting area is first calibrated by the reference method on the basis of the result of measurement in the reference area and then correction is made to remove from the result of measurement in the detecting area after the calibration the drift components extracted by a predetermined method from the result of measurement in the detecting area after the calibration, it is possible to first correct the result of measurement in the detecting area to remove therefrom the drift components extracted by a predetermined method from the result of measurement in the detecting area and then to correct the result of measurement in the reference area to remove therefrom the drift components extracted by a predetermined method from the result of measurement in the reference area and thereafter to calibrate the result of measurement in the detecting area after the correction by the reference method on the basis of the result of measurement in the reference area after the correction.

What is claimed is:

1. A measuring method comprising:

carrying out the measurement for a predetermined period in each of a detecting area in a film layer in which a ligand is fixed and a reference area of the film layer in which no ligand is fixed, calibrating a first result of the measurement in the detecting area on the basis of a second result of the measurement in the reference area, determining drift components from the first result after the calibration, and removing the drift components from the first result.

2. A measuring method as defined in claim 1 in which a predetermined method is used to perform the correcting in which a rate of change with time of a difference between an estimated result of the measurement and an actual result of the measurement is calculated for a part of a predetermined period and components which change at a rate of change are taken as the drift components, wherein the rate of change is calculated for a entire period of the predetermined period with a predetermined point in the predetermined period taken as a reference.

3. A measuring method comprising:

carrying out the measurement for a predetermined period in each of a detecting area of a film layer in which ligands are fixed and a reference area of the film layer in which no ligands are fixed, extracting first drift components from a first result of measurement in the detecting area, correcting the first result by removing the first drift components from the first result, extracting second drift components from a second result of measurement in the detecting area, correcting the second result by removing the second drift components from the second result, and calibrating the first result after the correction on the basis of the second result.

4. A measuring method as defined in claim 3 in which a predetermined method is used to perform the correcting in which a rate of change with time of a difference between an estimated result of the measurement and an actual result of the measurement is calculated for a part of a predetermined period and components which change at a rate of change are taken as the drift components wherein the rate of change is calculated for a entire period of the predetermined period with a predetermined point in the predetermined period taken as a reference.

5. A measuring system comprising a calibrating means operable to calibrate a result of a first measurement in a detecting area of a film layer having ligands fixed to it, the calibration being performed on a basis of a result of a second measurement in a reference area of the film layer having no ligands fixed to it, the first and the second measurement being carried out for a same predetermined period, and a correcting means operable to remove drift components from the first result after the calibration, the drift components being extracted from the first result.

6. A measuring system as defined in claim 5 in which the correcting means is operable to perform correction using a procedure in which a rate of change with time of a difference between an estimated result of the measurement and an actual result of the measurement is calculated for a part of a predetermined period and components which change at a rate of change are taken as the drift components wherein the rate of change is calculated for a entire period of the predetermined period with a predetermined point in the predetermined period taken as a reference.

7. A measuring system comprising a correcting means operable to correct a first result of measurement in a detecting area of a film layer having ligands fixed to it, the correcting being done to remove first drift components from the first result, the first drift components being extracted from the first result, the first correcting means further operable to correct a second result of measurement in a reference area of the film layer having no ligands fixed to it, the correcting being done to remove second drift components from the second result, the second drift components being extracted from the second result, and a calibrating means operable to calibrate the first result based on the second result.

8. A measuring system as defined in claim 7 in which the correcting means is operable to perform correction using a procedure in which a rate of change with time of a difference between an estimated result of the measurement and an actual result of the measurement is calculated for a part of a predetermined period and the components which change at a rate of change are taken as the drift components wherein the rate of change is calculated for a entire period of the predetermined period with a predetermined point in the predetermined period taken as a reference.

* * * * *